US00PP10232P

United States Patent [19]

Fear et al.

[11] Patent Number: Plant 10,232

[45] Date of Patent: Feb. 10, 1998

[54] APRICOT TREE CV. 'SUAPRIEIGHT'

[75] Inventors: Carlos D. Fear, Aptos; Bruce D. Mowrey, La Selva Beach; David W. Cain, Bakersfield, all of Calif.

[73] Assignee: Sun World, Inc., Bakersfield, Calif.

[21] Appl. No.: 694,160

[22] Filed: Aug. 8, 1996

[51] Int. Cl.[6] ..... A01H 5/00

[52] U.S. Cl. ..... Plt./39

[58] Field of Search ..... Plt./39

*Primary Examiner*—James R. Feyrer

*Attorney, Agent, or Firm*—Knobbe, Martens, Olson & Bear, LLP

[57] ABSTRACT

A new and distinct apricot tree variety characterized by its high productivity and its very large fruit which exhibits an intense red external blush.

1 Drawing Sheet

BACKGROUND AND SUMMARY OF THE INVENTION

This invention relates to the discovery and asexual propagation of a new variety of hybrid apricot tree, *Prunus armeniaca* cv. 'Suaprieight'. The variety produces a relatively large and very productive apricot, having excellent apricot flavor and an attractive external red blush, and cultivated for the fresh fruit market. It was discovered on Jun. 7, 1990 in Wasco, Kern County, Calif., the new variety being hybridized by Carlos D. Fear, and selected and evaluated by Bruce D. Mowrey and David W. Cain.

The variety has as its seed parent, Apricot tree cv. 'Suapritwo' (U.S. Plant Pat. No. 7,550), and its pollen parent is an unnamed, unpatented apricot tree seedling identified in the breeders' plant collection as seedling 066-245, which was derived as an open pollinated seedling of apricot selection S#3. The parent varieties were first crossed in February 1987, and the resulting seed was harvested and sowed in September 1987, with the date of first flowering being February 1990. The new 'Suaprieight' variety was first propagated by Bruce D. Mowrey in June 1990, at a ranch near Wasco, Kern County, Calif., by budding on Nemared rootstock.

The new variety cv. 'Suaprieigth' may be distinguished from other presently available commercial apricot tree cultivars by the following combination of characteristics: the fruit of the new 'Suaprieight' apricot variety is of a very large size and is extremely productive compared with most other commercial apricot varieties; it ripens in the late season about with the Patterson variety (U.S. Plant Pat. No. 2,877) and, thus, is usually eating ripe in Wasco, Calif. about June 7; but the fruit of 'Suaprieight' is of a much larger size, better flavor and exhibits a more intense red external blush than the Patterson variety.

The new variety may be distinguished from its pollen parent, seedling 066-245, by the following combination of characteristics: the fruit of the 'Suaprieight' ripens later, has lower acidity, a larger size and more rounded shape than seedling 066-245. The new variety may be distinguished from its seed parent, 'Suapritwo', by the following combination of characteristics: the 'Suaprieight' fruit outwardly resembles the fruit of the 'Suapritwo' variety in size and shape; however, it ripens 10 days later and has a slightly greener ground color. The new variety is further distinguished from 'Suapritwo' by being self fertile and much more productive than 'Suapritwo' in years having a low accumulation of winter chilling hours (hours of temperatures between 32° F. and 45° F.). The new 'Suaprieight' variety has been shown to maintain its distinguishing characteristics through successive asexual propagations by, for example, budding.

BRIEF DESCRIPTION OF THE FIGURE

The accompanying drawing in FIG. 1 illustrates, in full color, a typical stem and mature leaves of the new apricot tree variety, and the outer surface of ripe fruit as viewed perpendicular to the suture line plane and looking at the suture line. The drawing also illustrates the fruit of the new variety sectioned in half from end to end, with the stone removed from the flesh.

DETAILED BOTANICAL DESCRIPTION OF THE INVENTION

Figure 1:
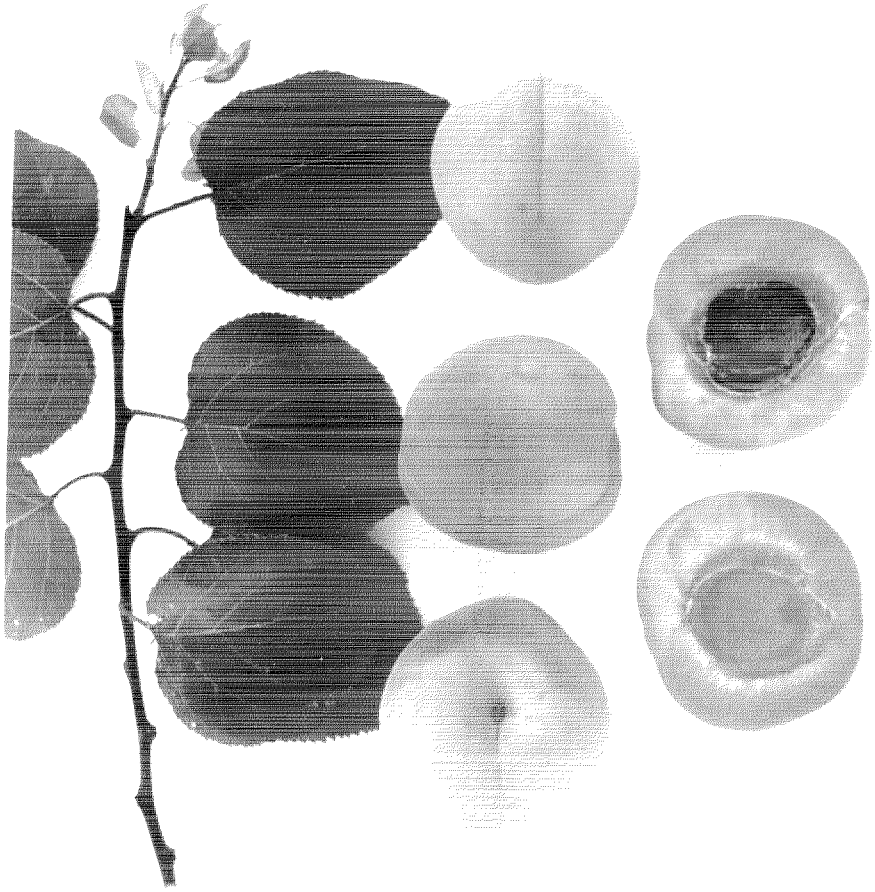

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

The descriptive matter which follows pertains to 'Suaprieight' plants grown in the vicinity of Wasco, Kern County, Calif., during 1994, and is believed to apply to plants of the variety grown under similar conditions of soil and climate elsewhere:

TREE

*Size.*—Large
*Vigor.*—Vigorous.
*Habit.*—Semi-upright.
*Density of foliage.*—Dense.
*Shape.*—Topped.
*Hardiness.*—Hardy, in Wasco, Calif.
*Productivity.*—Very productive.
*Fruit bearing.*—Regular bearer.
*Root stock.*—Nemared.

Trunk:
*Shape.*—Stocky.
*Surface texture.*—Medium.

Branches:
*Shape.*—Medium.
*Surface texture.*—Medium.
*Surface appearance.*—Semi-glossy.

Lenticels:
*Number.*—Numerous.
*Size.*—Large.

LEAVES

General:
*Average length.*—About 12.8 cm.
*Average width.*—About 7.8 cm.
*Size.*—Large.
*Outline.*—Spatulate.
*Profile.*—Up folded.
*Leaf blade tip.*—In the plane of the leaf.
*Angle of tip.*—Acute.
*Margin.*—Finely serrate.
*Undulation of margin.*—Slight.
*Apex.*—Acuminate.
*Base.*—U-shaped.
*Thickness.*—Medium.
Upper surface:
*Color.*—Green 137B.
*Glossiness.*—Weak.
*Pubescence.*—Absent.
*Surface texture.*—Smooth.
*Surface appearance.*—Dull.
Lower surface:
*Color.*—Green 137B.
*Glossiness.*—Weak.
*Pubescence.*—Absent.
*Surface texture.*—Smooth.
*Surface appearance.*—Dull.
Petiole:
*Length.*—Long.
*Thickness.*—Medium.
Glands:
*Average number.*—2.5.
*Positioning.*—(a) On petiole. (b) Alternate.
*Size.*—Medium.
*Shape.*—Globose.
*Color.*—Brown 200B.
Stipules:
*Persistence.*—Fall off.
Wood (leaf) buds:
*Shape.*—Rounded.
*Size.*—Very Small.
*Position relative to shoot.*—Held out.
*Support.*—Decurrent.
*Size.*—Small.
*Time of bud burst.*—Early.

FLOWERING SHOOTS

Anthocyanin coloration:
*Presence.*—Present.
*Intensity.*—Medium.
Thickness: Medium.
Internode length: Medium; about 1.4 cm.
Buds:
*Density: Sparase to medium.*
*Distribution: On spurs and one year old shoots.*
*Ratio of wood (leaf) buds to flowering shoots.*—1:1.5.

FLOWERS

General:
*Date of full bloom.*—Feb. 24, 1994.
*Time of bloom.*—Average, as compared with similar varieties in the growing area of Wasco, Calif.
*Duration of bloom.*—Medium to long.
*Size (fully opened flower).*—Medium; about 2.9 cm (diameter).
*Shape.*—Rosaceous.
*Petals.*—Overlapping.
*Color (fully opened flower).*—White 155D.
Flower-Buds:
*Hardiness.*—Hardy, in Wasco, Calif.
*Size.*—Medium.
*Length.*—Medium.
*Shape.*—Pointed; plump.
*Positioning.*—Free.
*Pubescence.*—Absent.
*Color.*—Greyed-Orange 166B.
Peduncle:
*Length.*—Medium.
*Thickness.*—Medium.
*Pubescence.*—Pubescent.
Receptacle:
*Depth.*—Shallow to medium.
*Pubescence of inner surface (at white bud stage).*—Absent.
*Pubescence of outer surface.*—Absent.
Sepals:
*Positioning.*—Touching receptacle.
*Shape.*—Triangular.
*Pubescence of inner surface.*—Absent.
*Pubescence of outer surface.*—Few to medium.
*Frequency of double sepals.*—Few.
Petals:
*Frequency of double petals.*—Sometimes has 6 petals.
*Size.*—Medium to large; about 1.3 cm. in width.
*Shape.*—Transverse broad elliptic.
*Claw length.*—Short.
*Margin waviness.*—Medium.
*Base angle.*—Wide.
*Division of upper margin.*—Entire.
*Pubescene of inner surface.*—Absent.
*Pubescence of outer surface.*—Absent.
*Color.*—inner surface: White 155D.
outer surface: White 155D.
Stigma:
*Position (as compared with anthers).*—Above.
Anthers:
*Color (just before dehiscence).*—Yellow-Orange 17B.
Pollen:
*Color.*—Yellow 13B.
Stamens:
*Position.*—Perigynous.
Pistil:
*Frequency of supplementary.*—Few.
*Number.*—Sometimes more than one.
Ovary:
*Pubescence.*—Pubescent.
*Density of hairs.*—Slight to medium.
Style:
*Pubescence (of base).*—Pubescent.
*Density of hairs.*—Slight.

FRUIT

General:
*Maturity when described.*—Eating-ripe.
*Date.*—Jun. 7, 1994.
*Size.*—Slightly variable; large.
*Axial diameter.*—About 6.2 cm.
*Transverse in suture plane.*—About 6.6 cm.
*At right angles to suture plane.*—About 6.5 cm.
*Form.*—Slightly variable; unsymmetrical to globose; oblong.
*Position of maximum diameter.*—Towards stem end.

*Symmetry about the suture.*—Asymmetric.
*Season ripening.*—Late.
*Use.*—Market; fresh.
*Keeping quality.*—Medium.
*Resistance to.*—Insects: Good, in Wasco, Calif. Diseases: Good, in Wasco, Calif.
*Shipping quality.*—Medium.

Suture: Extends from base to pistil point.

Ventral surface:
*Shape.*—Rounded slightly.
*Lips.*—Equal.
*Depression of apex.*—Distinct.
*Pistil base.*—Persisting.
*Pubescence of apex.*—Pubescent.
*Density of apex pubescence.*—Sparse.

Stem cavity:
*Shape.*—Flaring; elongated in suture plane; with suture showing on one side.
*Depth.*—About 1.0 cm.
*Breadth.*—About 2.4 cm.
*Markings.*—None.

Base:
*Shape.*—Rounded; truncate.

Apex:
*Shape.*—Rounded to truncate.

Pistil point:
*Shape.*—Apical; slightly depressed.

Stem:
*Length.*—About 0.8 cm; medium; pubescent.
*Adherence to stone.*—Medium.

Skin:
*Thickness.*—Medium.
*Texture.*—Medium.
*Reticulation.*—Present.
*Roughness.*—Present.
*Tenacity.*—Tenacious to flesh.
*Tendency to crack.*—Slight in wet season.
*Color.*—Orange 24A.
*Over-Color (blush).*—Red 45A.
*Down (pubescence).*—Scant.
*Bloom.*—Absent.

Flesh:
*Color.*—Orange 25A.
*Surface of the pit cavity.*—Orange 25A.
*Amygdalin.*—Wanting.
*Juice.*—Moderate.
*Sugar content.*—Medium to high.
*Texture.*—Medium; soft; melting.
*Fibers.*—Abundant; tender.
*Ripens.*—Earliest at apex;
*Flavor.*—Vinous.
*Aroma.*—Distinct.
*Eating quality.*—Good.
*Ratio of stone to flesh.*—About 6.2:138 grams.

STONE

General:
*Adherence to flesh.*—Free.
*Fibers.*—Retains short fibers; like threads along ridges.
*Size.*—Large.
*Length.*—About 3.1 cm.
*Breadth.*—About 3.0 cm.
*Width of stalk end.*—About 0.55 cm.
*Angle of stalk end.*—Obtuse.
*Thickness: About* 1.45 cm.
*Form (profile).*—Oval.
*Form (ventral view).*—Sub-globular.
*Base.*—Oblique.
*Hilum.*—Narrow; oblong.
*Apex.*—Rounded.
*Position of maximum breadth.*—Towards middle.
*Sides.*—
*Surface.*—Irregularly pitted throughout.
*Outgrowing keel.*—Well developed.
*Ridges.*—Continuous.
*Pits.*—Angular.
*Ventrical edge.*—Medium to thick.
*Dorsal edge.*—Medium.
*Color of dry stone.*—Greyed-Orange 164B.
*Tendency to split.*—Slight in wet season.

We claim:

1. A new and distinct variety of apricot tree cv. 'Suaprieight' as herein illustrated and described.

* * * * *